United States Patent [19]

Gross et al.

[11] Patent Number: 5,527,288
[45] Date of Patent: Jun. 18, 1996

[54] INTRADERMAL DRUG DELIVERY DEVICE AND METHOD FOR INTRADERMAL DELIVERY OF DRUGS

[75] Inventors: Joseph Gross; John G. Kelly, both of Rathgar, Ireland

[73] Assignee: Elan Medical Technologies Limited, Athlone, Ireland

[21] Appl. No.: 183,482

[22] Filed: Jan. 18, 1994

Related U.S. Application Data

[63] Continuation-in-part of Ser. No. 981,652, Nov. 25, 1992, Pat. No. 5,279,544, which is a continuation-in-part of Ser. No. 850,595, Mar. 13, 1992, abandoned, which is a continuation-in-part of Ser. No. 627,104, Dec. 13, 1990, Pat. No. 5,156,591.

[30] Foreign Application Priority Data

Nov. 18, 1993 [IE] Ireland ................................. 930882

[51] Int. Cl.⁶ ................................................. A61M 37/00
[52] U.S. Cl. ............................................. 604/140; 604/145
[58] Field of Search ...................................... 604/140–143, 604/145, 147, 890.1, 892.1

[56] References Cited

U.S. PATENT DOCUMENTS

| | | | |
|---|---|---|---|
| 3,923,060 | 12/1975 | Ellinwood et al. | 128/260 |
| 4,140,117 | 2/1979 | Buckles et al. | 128/213 |
| 4,522,622 | 6/1985 | Peery et al. | 604/191 |
| 4,734,092 | 3/1988 | Millerd | 604/140 X |
| 4,753,651 | 6/1988 | Eckenhoff | 424/449 |
| 4,886,499 | 12/1989 | Cirelli et al. | 604/145 X |
| 5,090,963 | 2/1992 | Gross et al. | 604/145 X |
| 5,156,591 | 10/1992 | Gross et al. | 604/20 |
| 5,279,544 | 1/1994 | Gross et al. | 604/20 |
| 5,318,557 | 6/1994 | Gross | 604/141 X |
| 5,354,264 | 10/1994 | Bae et al. | 604/145 x |

FOREIGN PATENT DOCUMENTS

| | | | |
|---|---|---|---|
| 0513879A2 | 11/1992 | European Pat. Off. | A61M 37/00 |
| 60868 | 8/1994 | Switzerland | A61M 5/20 |
| WO91/00753 | 1/1991 | WIPO | A61M 31/00 |
| WO92/11879 | 7/1992 | WIPO | A61M 1/08 |
| WO93/17754 | 9/1993 | WIPO | A61N 1/30 |

*Primary Examiner*—William E. Kamm
*Assistant Examiner*—Jeffrey R. Jastrzab
*Attorney, Agent, or Firm*—Mary L. Severson

[57] ABSTRACT

An intradermal drug delivery device for delivering a liquid drug to a subject via the subject's skin includes a housing having a lower surface provided with an adhesive coating for adhering the housing to the subject's skin. An expansible-contractible chamber within the housing defines a reservoir which is expanded upon being filled with the drug and contracted to dispense the drug. A hollow needle extends through the lower surface of the housing and has an inner end which communicates with the reservoir and an outer end which projects outwardly of the housing a short distance to penetrate through the epidermis and into the dermis of the subject's skin when the housing is adhered thereto. The device permits delivery of drugs of relatively large molecular size and at slow rates which can be precisely controlled. A method of delivering a liquid drug intradermally includes adhering the intradermal delivery device to the skin of the subject and activating the means for actively discharging the at least one drug from the reservoir to the subject's skin via the needle.

37 Claims, 8 Drawing Sheets

INTRADERMAL DRUG DELIVERY DEVICE AND METHOD FOR INTRADERMAL DELIVERY OF DRUGS

RELATED APPLICATIONS

The present application is a continuation-in-part of our patent application Ser. No. 07/981,652, filed Nov. 25, 1992, now U.S. Pat. No. 5,279,544, which in turn is a continuation-in-part of our patent application Ser. No. 07/850,595, filed Mar. 13, 1992, now abandoned, which in turn is a continuation-in-part of our patent application Ser. No. 07/627,104, filed Dec. 13, 1990, now U.S. Pat. No. 5,156,591.

BACKGROUND OF THE INVENTION

The present invention relates to drug delivery devices, and in particular to an intradermal drug delivery device for delivering a liquid drug to a subject via the subject's skin.

One type of transdermal drug delivery device is in the form of a patch applied to the subject's skin and containing a drug penetrating the skin by osmosis and/or by a controlled mass transport phenomenon such as iontophoresis. Simple patches, however, provide no control, or limited control, of the rate of drug delivery, which depends on skin conditions, the nature (particularly molecular size) of the drug to be delivered, and the like. Iontophoresis devices are also not entirely satisfactory in their ability to deliver large molecules and to control the rate of delivery thereof. All such devices are limited by the barrier function of the skin.

Another transdermal drug delivery device is described in International Patent Publication WO 93/17754. In one embodiment this device comprises a housing containing a liquid reservoir and a drug delivery body carded by the housing and engageable with the subject's skin. The drug delivery body carries a plurality of hollow needles (of which there are preferably at least fifty) having an outer diameter of the order of 1 mm, which needles are designed to pierce the outer layer of dead cells (the stratum corneum) of the skin, thereby enhancing the penetration of the drug through the skin.

However, certain disadvantages are associated with this method of drug delivery. Firstly, there is a risk of considerable pain and traumatization of the skin associated with the application of the particular array of needles. Secondly, the drug may leak out around the entry point of each needle as a result of the pressure being applied to assist the delivery of the drug. A film of liquid drug covering the area of application may cause irritation for subjects with sensitive skin; certain drugs may aggravate this irritation. The leakage also results in a lower efficiency of drug delivery. Thirdly, it can be difficult to ensure that the device is correctly applied with the tips of the needles penetrating the stratum corneum. The skin has a natural resilience and elasticity. The device is pressed onto the skin such that the entire area of the needle arrangement depresses the surface of the skin, even when considerable pressure is applied. For this reason, an extra degree of pain is associated with the correct application of the device, due to the amount of force needed to properly pierce the stratum corneum with all of the needles.

BRIEF SUMMARY OF THE INVENTION

According to the present invention, there is provided an intradermal drug delivery device for delivering a liquid drug to a subject via the subject's skin, comprising: a housing having a lower surface for application to the skin of the subject; means for affixing the housing in position with the lower surface in contact with the subject's skin; a drug reservoir within the housing; a single hollow needle associated with the drug reservoir extending through the lower surface, having an inner end communicating with the drug reservoir and an outer end projecting outwards a sufficient distance so as to penetrate through the epidermis and into the dermis when the housing is pressed against the skin; and means for actively discharging the drug from the reservoir to the subject's skin via the needle; the lower surface being shaped such that when pressed against the skin, a substantial proportion of the pressure applied to the skin is directed through the needle tip; and the needle having an outer diameter 0.2 mm or less.

According to the preferred embodiments described below, the needle projects outwardly of the housing approximately 0.3–3.0 mm, most preferably 0.3–1.0 mm, and has an outer diameter of 0.1–0.2 mm and an inner diameter of 0.05–0.075 mm.

As will be described more particularly below, such an intradermal drug delivery device permits the delivery of a variety of drugs including drugs of relatively large molecular size, and at slow rates which can be precisely controlled.

According to further features of the invention described below, the drug reservoir may be an expansible-contractible chamber which is expanded upon being filled with the drug and is contracted to dispense the drug therefrom at controlled rates by the means for actively discharging the drug. These means can include an electrically-controlled gas generator, such as an electrolytic cell, a prestressed spring or membrane, or osmotic means to provide for osmosis between a pure water compartment and a saline compartment included within the housing.

According to another aspect of the invention, there is provided a drug delivery device having a plurality of drug reservoirs within the housing, all drug reservoirs communicating with an outlet cavity with which the single hollow needle also communicates, and means such as electrical means for individually controlling the feeding of drug from the plurality of reservoirs to the outlet cavity.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

The device according to the invention overcomes the disadvantages indicated above for the following reasons: Firstly, since only a single needle is generally used, only a single point of entry is associated with the application of the device, eliminating most of the pain and trauma resulting form the application of the device. In addition, the extremely narrow diameter of the single needle allows the application to be virtually painless and minimally invasive.

Secondly, the amount of leakage is diminished to a very large extent, if not totally. The delivery is far more controlled as a result. The leakage is reduced for two reasons: (i) the drug is delivered below the epidermis (and not just to below the stratum corneum); and (ii) only a single point exists at which leakage might occur.

Thirdly, the shape of the lower surface results in a substantial proportion of the pressure being directed through the needle tip. If the device is not correctly shaped, too much pressure may be directed through the lower surface so that the skin is stretched by the surface of the device and not the needle. According to the invention, the needle must provide sufficient pressure to stretch and pierce the epidermis, i.e., the elasticity of the skin must be directed against the needle. It should be noted that the effective pressure (force applied to the housing per unit area of skin contact) is, for a given tome, far higher for the device according to the invention, since the effective area of application is diminished approximately fifty-told when only one needle is applied as opposed to 50 needles, and is further reduced as a result of the narrow diameter needle used.

Since the intradermal device of this invention delivers the drug below the epidermis. i.e., to the interface between the epidermis and the dermis or to the interior of the dermis or subcutaneously, many of the problems of transdermal application are non-existent; the drug is delivered directly to a capillary-containing tissue and has no barriers to pass through before entering the vascular system.

Preferably, the means for holding the housing in position comprises a pressure-adhesive coating, such as an acrylate adhesive, on the lower surface thereof. When the device is pressed against the skin, the needle penetrates the epidermis and the pressure-adhesive coating affixes the lower surface to the skin. A single-step, painless and trauma-free application is thus provided by the invention. Additionally or alternatively, the device may be held in position by a strap or bracelet.

According to one embodiment of the invention, the lower surface of the housing has a convex shape and the hollow needle extends from the center of the convexity. Alternatively, the lower surface of the housing is provided with a protuberance from which the needle projects. In a further alternative, the lower surface of the housing is of a conical shape and the hollow needle extends from the apex of the cone. In a further embodiment, the lower surface of the housing can have a convex shape and also be provided with a protuberance from which the needle projects.

In each case, the needle is positioned to engage the skin directly so that it pierces the skin before a large part of the surface has made contact. In effect, parts of the surface distal from the needle are held back from the skin as a consequence of the shape of the lower surface. For this reason, much of the pressure which might have been applied by the surface of a flat device is instead directed through the needle tip.

The device may however have a flat surface provided that the size of the device or the shape and elasticity of the skin to which the device is to be applied enables a substantial portion of the pressure to be directed through the needle tip.

Preferably, the needle projects outwards of the housing by approximately 0.3–3.0 mm, most preferably 0.3–1.0 mm, and has an outer diameter of 0.1–0.2 mm and an inner diameter of 0.05–0.075 mm. Such a needle is relatively painless to apply, causes little or no trauma to the skin and yet allows precisely controllable delivery of a liquid drug, including drugs of relatively large molecular size.

Preferably, the reservoir is in the form of an expansible-contractible chamber which is expanded when filled with the drug and which can be contracted to dispense the drug therefrom.

Further, preferably, the drug reservoir, when filled, has a volume of 0.2–10.0 ml or larger, more preferably 0.3–6.0 ml, most preferably 0.5 to 3.0 ml.

Further, preferably, the means for actively discharging the drug comprises an electrically controlled gas generator within the housing for generating a gas to contract the drug reservoir in order to discharge the drug therefrom.

Such an intradermal delivery device provides precise control over the rate of delivery of the drug; in particular, it allows the drug to be delivered at precisely controllable slow rates. The use of a narrow needle is also advantageous for achieving slow rates of delivery, while still allowing the delivery of a variety of drugs, including those of relatively large molecular size.

Suitably, the gas generator is an electrolytic cell. In a preferred embodiment of the invention, the device further comprises a start button which is depressible in order to activate the means for actively discharging the drug from the drug reservoir, such as a start button which energizes a gas generator. Thus, the device may be supplied and stored for an indefinite period of time and yet be immediately activated when required.

Suitably, the device comprises an electronic circuit for controlling the time and rate of gas generation, thereby controlling the discharge of the drug from the drug reservoir. Preferably, the electronic circuit comprises a microprocessor which is programmable with respect to the time and rate of gas generation. For instance, the microprocessor can be programmed to deliver the liquid drug in a continuous infusion, in a pulsatile manner or in intermittent doses as well as in response to input from the subject, such as patient controlled analgesia.

It is thus possible to choose or devise a dosage regime which will suit the requirements both of the individual patient and of the drug to be delivered. For example, the device may comprise a microprocessor which controls the delivery such that the rate of delivery is varied during a 24 hour cycle as is necessary due to the differing requirements of drug dosage during periods of activity, inactivity and sleep, and taking account of the subject's requirements in relation to food intake.

Alternatively, the subject might be provided with separate daytime and nighttime devices, each having a different electronic circuit for controlling the time and rate of drug delivery.

It may be desirable to automatically deliver certain drugs only when required by the subject, either by patient activation or passively, such as by a feedback mechanism. In such a case, there is provided a device wherein the housing further includes a sensor (feedback) for detecting a condition in the body of the subject and for controlling the delivery of the drug in response thereto. The sensor may be, for example, a temperature sensor, a pulse rate sensor, a blood glucose sensor, a blood pressure sensor or a pH sensor.

Thus, where a device is intended to deliver a fever-reducing drug, for example, it might be provided with a temperature sensor such that a detected increase in body temperature above a certain value would activate the drug delivery or increase the rate of drug delivery.

The sensor may rest against the skin, may be inserted through the skin, or may be within the device and separate from the skin.

According to one embodiment of the invention, the housing includes a plurality of drug reservoirs, each reservoir being contractible by a separate gas generator and communicating with an outlet cavity with which the single hollow needle also communicates. In one such embodiment, all of the drug reservoirs communicate in series with the outlet cavity. In an alternative embodiment, all of the drug reservoirs communicate in parallel with the outlet cavity.

Including a plurality of drug reservoirs provides for considerable variations in the amounts of drug which can be delivered, in the rates at which drug can be delivered and in the number of drugs which can be delivered by the same device. The provision of a plurality of reservoirs allows the device to be used in a range of situations for which a single reservoir device would be unsuitable.

A preferred embodiment of a device which is to deliver more than one drug has a housing which includes a plurality of drug reservoirs, each having a single hollow needle associated therewith. Such a device is especially suitable when the drugs am not suitable to mix with one another or when they are to be delivered separately or sequentially.

In an alternative embodiment of a device according to the invention wherein the reservoir is in the form of an expansible-contractible chamber, the means for actively discharging the drug comprises a spring which is stressed by the expansion of the drug reservoir upon filling it with a drug, and which tends to return to its unstressed condition to contract the reservoir and thereby to discharge the drug via the hollow needle.

In another alternative embodiment wherein the reservoir is in the form of an expansible-contractible chamber, the means for actively discharging the drug comprises a membrane which is stressed by the expansion of the drug reservoir upon filling it with a drug, and which tends to return to its unstressed condition to contract the reservoir and thereby to discharge the drug via the hollow needle.

Either of the last mentioned alternative embodiments provide for devices which can be reusable when provided with means for refilling the drug reservoir. This refilling may take place either upon removal of the device or in situ.

In another alternative embodiment of the device according to the invention, the means for actively discharging the drug comprises a deformable liquid-impermeable membrane and a rigid liquid-permeable membrane; one side of the deformable liquid-impermeable membrane defining one side of the drug reservoir; the opposite side of the deformable liquid-impermeable membrane and one side of the rigid liquid-permeable membrane defining a saline reservoir for receiving a saline solution; the opposite side of the rigid liquid-permeable membrane defining, with a rigid part of the housing, a pure water reservoir for receiving pure water to expand the saline reservoir by osmosis, thereby to contract the drug reservoir in order to dispense the drug therefrom via the hollow needle.

Such a device provides for a predictable and continuous delivery of the liquid drug, whose rate of delivery can be chosen according to the volume, concentration and nature of the saline solution used, since the expansion of the saline reservoir (and thus the contraction of the drag reservoir) depends on the osmotic pressure across the membrane separating the pure water reservoir from the saline reservoir.

Figure 14:
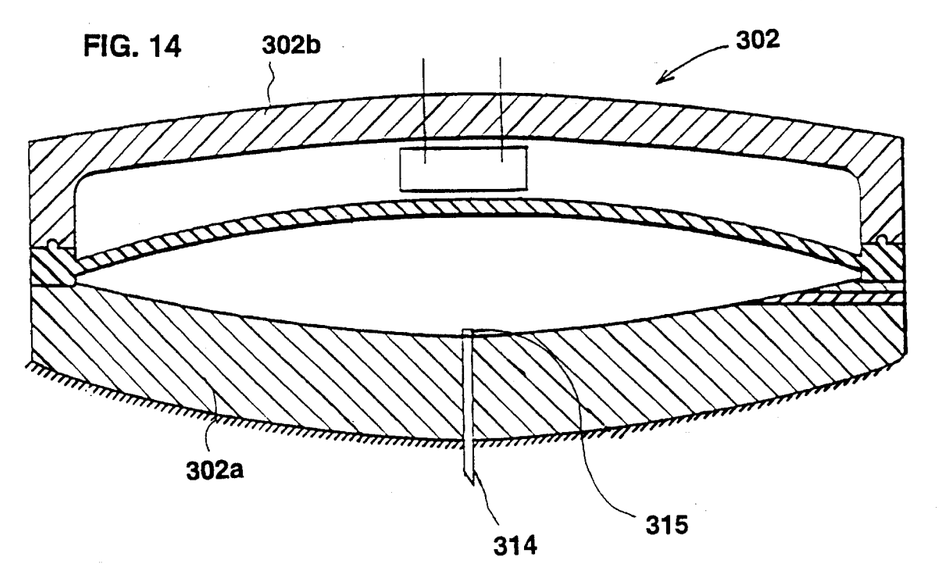
FIG. 14 illustrates the membrane which is permeable to the liquid drug and impermeable to solid impurities covering the inner end of the hollow needle for one embodiment according to the present invention.

Preferably, as shown in FIG. 14, the device further comprises a membrane which is permeable to the liquid drug and impermeable to solid impurities, the membrane covering the inner end of the hollow needle. The advantage of the membrane covering the inner end of the hollow needle is to filter out solid particles to prevent clogging of the needle. Preferably, the pore size of this membrane may range from 0.2 μm to 1.0 μm.

The present invention also encompasses a method of delivering a biologically effective amount of a liquid drug intradermally to an animal subject, especially a human, comprising the steps of: (1) affixing an intradermal drug delivery device to the skin of the subject, the drug delivery device including a housing having a lower surface for application to the skin of the subject; means for affixing the housing in position with the lower surface in contact with the subject's skin; a drug reservoir within the housing and containing a biologically effective amount of at least one liquid drug; a single hollow needle associated with the drug reservoir having an outer diameter of 0.2 mm or less and extending through the lower surface and having an inner end communicating with the drug reservoir and an outer end projecting outwards a sufficient distance so as to penetrate through the epidermis and into the dermis when the housing is affixed to the skin; and means for actively discharging the at least one drug from the reservoir to the subject's skin via the needle; and (2) activating the means for actively discharging the at least one drug to deliver a biologically effective amount of the at least one drug to the subject.

As used herein, the term, "liquid drug," is meant to encompass any drug-containing fluid capable of being passed through the hollow needle in a controlled manner, such as a liquid, solution, gel or fine suspension. There is essentially no limitation on the type of liquid drug which can be used with the invention other than to exclude those liquid drugs which would be inappropriate to deliver to the subject intradermally or subcutaneously. Representative drugs include peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and antidiuretic agents.

Typical drugs include peptides, proteins or hormones such as insulin, calcitonin, calcitonin gene regulating protein, atrial natriuretic protein, colony stimulating factor, betaseton, erythropoietin (EPO), interferons such as α, β or γ interferon, somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, pavefin, and analogues thereof; anti-migraine agents such as sumatriptan, ergot alkaloids, and analogues thereof; anti-coagulant agents such as hepafin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as 5-fluorouracil, bleomycin, and analogues thereof; prostaglandins and analogues thereof; and chemotherapy agents such as vincristine, and analogues thereof.

Figure 1:
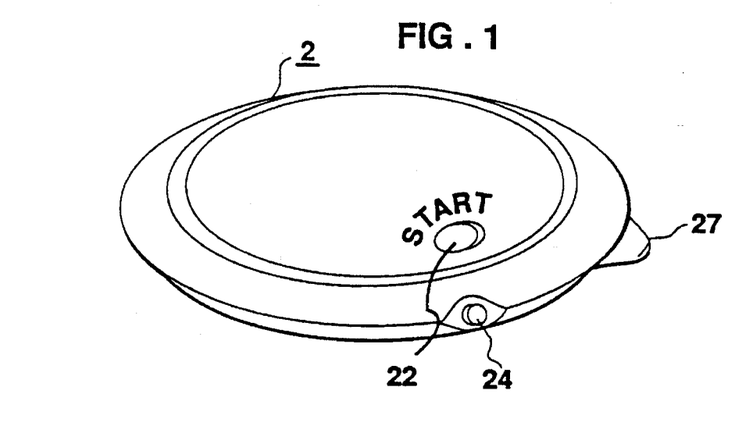
FIG. 1 illustrates one form of an intradermal drug delivery device constructed in accordance with the present invention.
Figure 2:
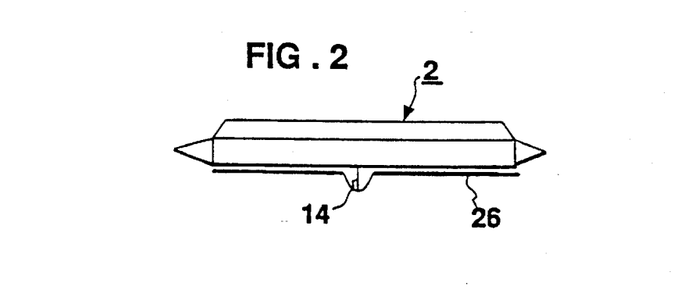
FIG. 2 is a side elevational view of the device of FIG. 1.
Figure 3:
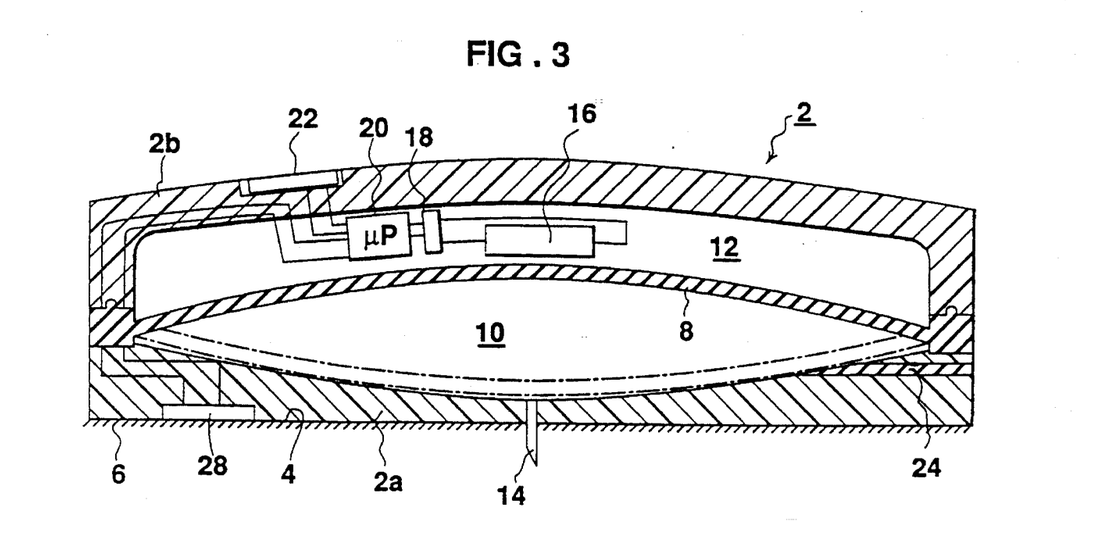
FIG. 3 is an enlarged longitudinal sectional view of the device of FIG. 1.

THE EMBODIMENT OF FIGS. 1–3

The intradermal drug delivery device illustrated in FIGS. 1–3 includes a housing 2 of disc or cylindrical configuration having a flat lower surface 4 coated with a pressure-sensitive adhesive 6 for adhering the housing to the skin of the subject to receive the drug. The interior of housing 2 includes a flexible liquid-impermeable membrane 8 defining an expansible/contractible chamber 10 between it and the lower section 2a of housing 2, and a second expansible/contractible chamber 12 between it and the upper section 2b of the housing. Chamber 10 serves as a reservoir for receiving the drug to be delivered, whereas chamber 12 serves as a gas chamber for controlling the delivery of the drug from the reservoir 10.

A hollow needle 14 extends through housing section 2a. The inner end of needle 14 communicates with the drug reservoir 10, whereas the outer end of the needle projects outwardly of the flat surface 4 of the housing a short distance so as to penetrate the epidermis of the subject's skin when the housing is applied and adhered thereto. Preferably, hollow needle 14 projects outwardly of the flat surface 4 a distance of 0.3–1.0 mm, just sufficient to penetrate through the epidermis of the subject's skin. The outer diameter of the needle is preferably from 0.1–0.2 mm and its inner diameter is preferably from 0.05–0.075 mm. These dimensions permit a slow, precisely-controllable delivery of the drug from the drug reservoir 10. The inner end of the hollow needle 14 may be covered by a filter membrane to prevent clogging particles from entering the needle.

The rate and time of delivery of the drug is controlled by a gas-generator 16 within the gas compartment 12. Preferably, gas generator 16 is an electrolytic cell energized by a battery 18 and controlled by a microprocessor 20 when actuated by a START button 22 mounted on housing section 2b.

Housing section 2a further includes an injection plug 24 which may be pierced by a syringe needle, for example, in order to fill reservoir 10 with the drug to be dispensed. In addition, the adhesive coating 6 on the flat lower surface 4 of housing section 2a is normally covered by a protective strip 26 (FIG. 2) which is peeled away when the device is to be used. Protective strip 26 preferably includes a tab extension 27 (FIG. 1) to facilitate removing the strip.

Optionally, housing section 2a further includes a sensor 28 flush with surface 4 so as to be pressed against the skin of the subject when the device is applied to the subject and held by the adhesive coating 6. For instance, sensor 28 may be a temperature sensor for sensing the temperature of the subject and for controlling microprocessor 20, and thereby the dispensing of the drug, in response to the subject's temperature. Sensor 28 may be a pulse rate sensor for sensing the pulse rate of a subject and for controlling, via processor 20, the dispensing of the drug in response thereto.

It will be seen that the device illustrated in FIGS. 1–3 may be used in the following manner.

Drug compartment 10 is filled with the drug to be dispensed by injecting same via syringe needle through the injection plug 24, thereby expanding the drug reservoir 10, e.g., to the full-line position shown in FIG. 3. Microprocessor 20 is preprogrammed according to the desired time and rate of delivery of the drug. Protective strip 26 is removed to expose the hollow needle 14, and the device is then pressed against the subject's skin such that the needle 14 penetrates only through the epidermis. The adhesive coating 6 firmly adheres the device to the subject's skin.

When the delivery is to start, the START button 22 is depressed. This energizes the electrolytic cell 16 to generate a gas under the control of microprocessor 20. This increases the pressure within gas chamber 12, thereby deforming membrane 8 to contract the drug chamber 10, to teed the drug from chamber 10 to the subject via the hollow needle 14 at a rate dependent on the rate of generation of the gas by the gas generator 16. This rate is controlled by the microprocessor 20.

The sensor 28 senses a predetermined condition of the subject and controls the delivery of the drug from reservoir 10 in accordance therewith. For example, sensor 28 may be a temperature sensor, for controlling the delivery of a fever-reducing drug; alternatively, it could be a pulse rate sensor or a blood pressure sensor for controlling the delivery of a drug appropriate to the sensed condition.

Figure 4:
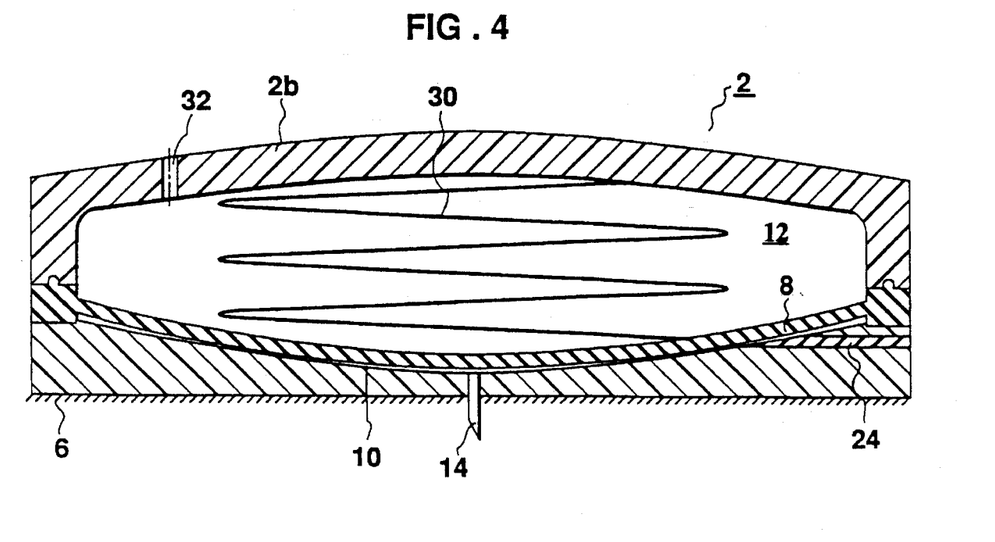
FIGS. 4, 5 and 6 are longitudinal sectional views illustrating other intradermal drug delivery devices constructed in accordance with the invention.

THE EMBODIMENT OF FIG. 4

FIG. 4 illustrates a similar device as FIGS. 1–3, and therefore corresponding parts have been identified by the same reference numbers. In the construction illustrated in FIG. 4, however, the drug reservoir 10 is contracted to feed the drug via the hollow needle 14, not by a gas generator as in FIGS. 1–3, but rather by a spring 30 included in compartment 12 between the diaphragm 8 and the housing section 2b. The latter section is formed with an atmospheric vent 32.

The device illustrated in FIG. 4 is used in the same manner as described above with respect to FIGS. 1–3, except that, instead of effecting the delivery of the drug by means of a gas generator under the control of a microprocessor as in FIGS. 1–3, the delivery of the drug is effected by spring 30 which is prestressed upon introducing the drug into reservoir 10 via the injection plug 24.

Figure 5:
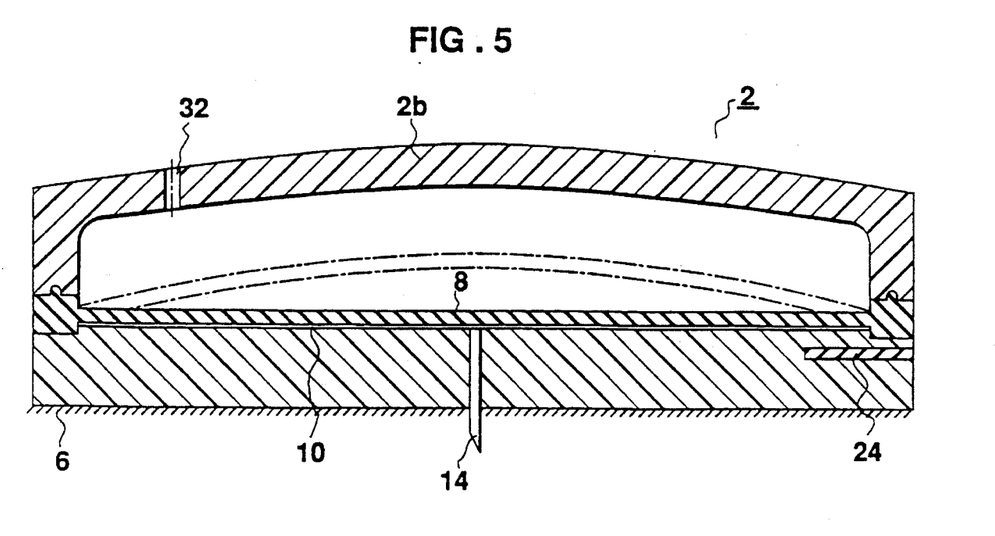

THE EMBODIMENT OF FIG. 5

The device illustrated in FIG. 5 is similar to that of FIG. 4, and therefore its corresponding parts are identified by the same reference numbers. In the device of FIG. 5, however, instead of including a spring (30) which is stressed upon filling the chamber 10 with the drug, the diaphragm 8 is made of an elastic material which is prestressed when so filling the drug chamber, and thereby effects the delivery of the drug via the hollow needle 14.

Figure 6:
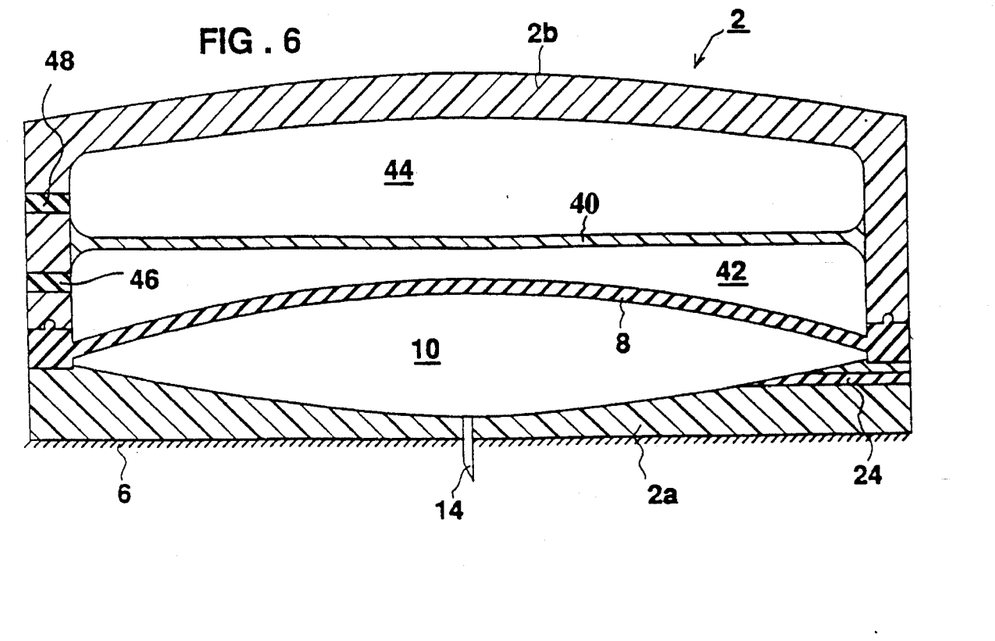

THE EMBODIMENT OF FIG. 6

FIG. 6 illustrates another device similar to those described earlier, and therefore the corresponding parts are also identified by the same reference numerals. In this case, however, the housing 2 includes not only the deformable liquid-impermeable membrane 8, but also a rigid liquid-permeable membrane 40. Thus, one side of the impermeable membrane 8 defines with housing section 2a the drug reservoir 10, whereas the other side of membrane 8 defines, with one side of the rigid liquid permeable membrane 40, a saline chamber 42. The other side of the permeable membrane 40 defines with housing section 2b a pure water chamber 44. Drug reservoir 10 may be filled as described above via the injection plug 24. The saline chamber 42 may be filled via another injection plug 46, and the pure water chamber 44 may be filled via another injection plug 48.

It will be seen that when the three chambers 10, 42 and 44 are filled as described above, water from chamber 44 will permeate by osmosis through membrane 40 into the saline chamber 42, thereby expanding that chamber and contracting the drug reservoir 10, forcing the drug out through the hollow needle 14.

Figure 7:
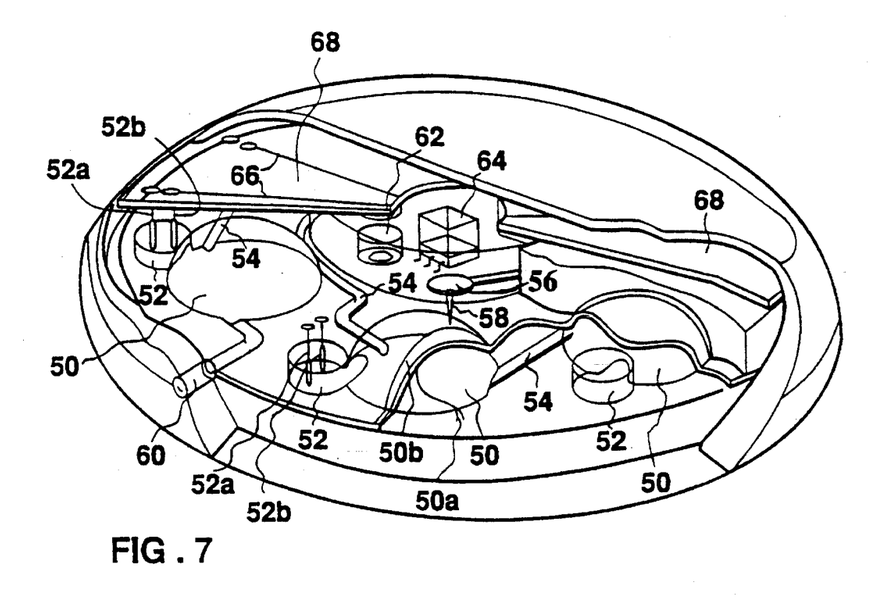
FIG. 7 is a diagrammatic view illustrating a multi-reservoir intradermal drug delivery device in accordance with the invention.
Figure 8:
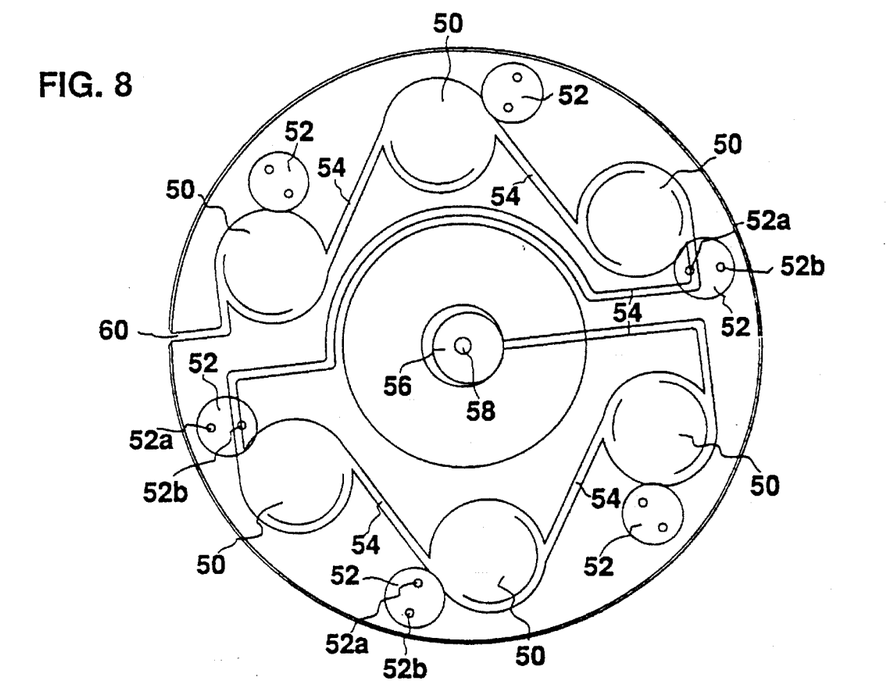
FIG. 8 is a top plan view more particularly illustrating the internal structure of the device of FIG. 7.

THE EMBODIMENT OF FIGS. 7 AND 8

FIGS. 7 and 8 illustrate a device similar to that of FIGS. 1–3, except that the device includes a plurality of separate drug reservoirs 50 (six being shown in FIG. 8 for example), each individually controlled by a gas generator 52. All the drug reservoirs are connected in series via conduits 54 to a central outlet cavity 56 with which the hollow needle 58 communicates. An injection plug 60 may be used for filling all the reservoirs 50 in series.

Each of the gas generators 52 is a separate electrolytic cell including a pair of electrodes 52a, 52b for applying electrical current to an electrolyte within the cell, thereby generating a gas within the cell corresponding to the electrical current applied. The so-generated gas is applied to the gas chamber of its respective drug reservoir 50, i.e., between a displaceable diaphragm 50a (FIG. 7) and a rigid cover 50b, to thereby contract the drug reservoir and to feed its drug via its conduit 54 to the outlet cavity 56, which is in communication with the injection needle 58.

The electrolytic cells 52 are energized by a battery 62 (FIG. 7) under the control of a microprocessor 64 via electrical conductors 66 carded by a printed circuit board 68 connected to the electrodes 52a, 52b of each electrolytic cell.

It will be seen that including a plurality of drug reservoirs 50 each separately controllable by its own gas generator 52, enables the device to be controlled to provide a wide range of dispensing rates. The series connections of the drug reservoirs with the outlet cavity 56, which is in communication with the injection needle 58 permits the device to be conveniently primed by injecting the drug via injection plug 60 into all the reservoirs in series until the drug begins to discharge through the needle.

Figure 9:
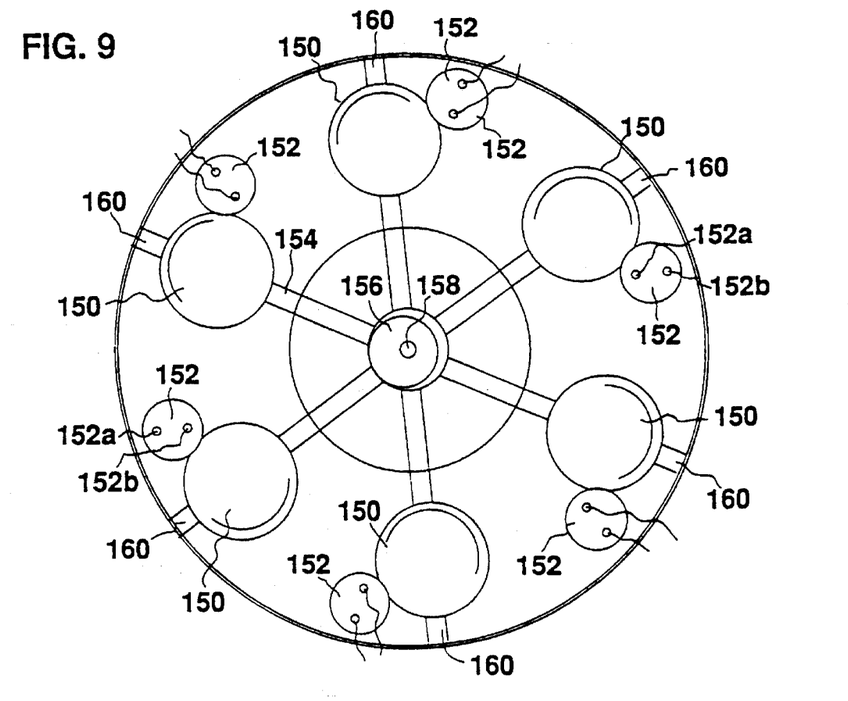
FIG. 9 is a view corresponding to that of FIG. 8, but showing a modification wherein the drug reservoirs are connected in parallel with the outlet cavity rather than in series as in FIG. 8.

THE EMBODIMENT OF FIG. 9

FIG. 9 illustrates a variation in the construction of the device of FIGS. 7 and 8, in that the plurality of drug reservoirs, therein designated 150, are connected, via their respective conduits 154, to the outlet cavity 156, which is in communication with the injection needle 158. As in the device of FIGS. 7 and 8, the device of FIG. 9 is also provided with a separate gas generator 152, e.g., an electrolytic cell, for each of the plurality of drug reservoirs 150. Each reservoir is separately filled via its own injection plug 160.

It will be seen that the device illustrated in FIG. 9 permits the delivery of a single drug, or a mixture of drugs, all under the control of the microprocessor (e.g., 64, FIG. 7). Thus, if a large quantity of drug is to be delivered, the microprocessor could be preprogrammed to energize a plurality of the electrolytic cells 152 at one time; and if two or more drugs are to be simultaneously delivered, the various reservoirs 150 would be filled with the respective drugs and dispensed as required under the control of the microprocessor.

Figure 10:
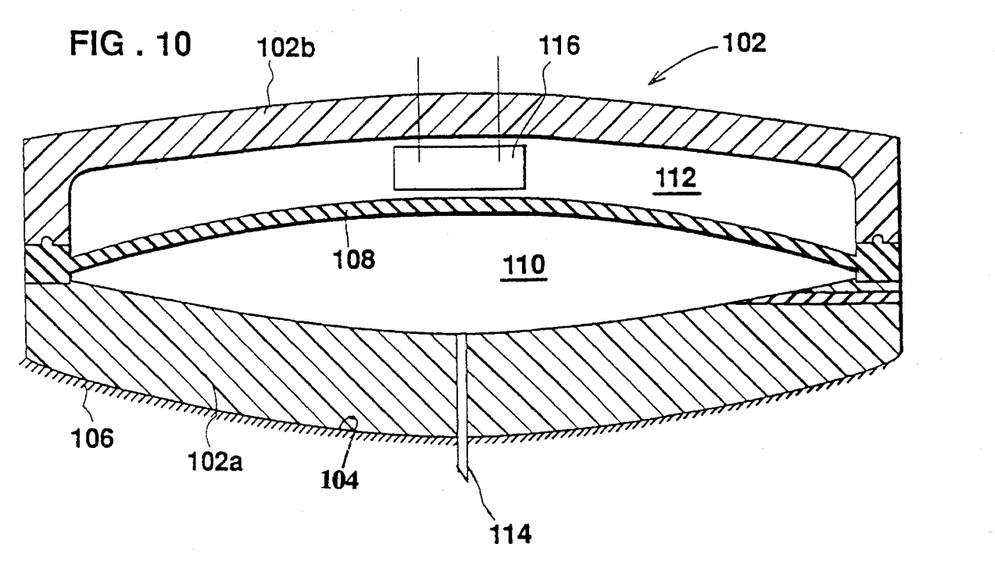
FIGS. 10 and 11 illustrate two further variations in the construction of the device.
Figure 11:
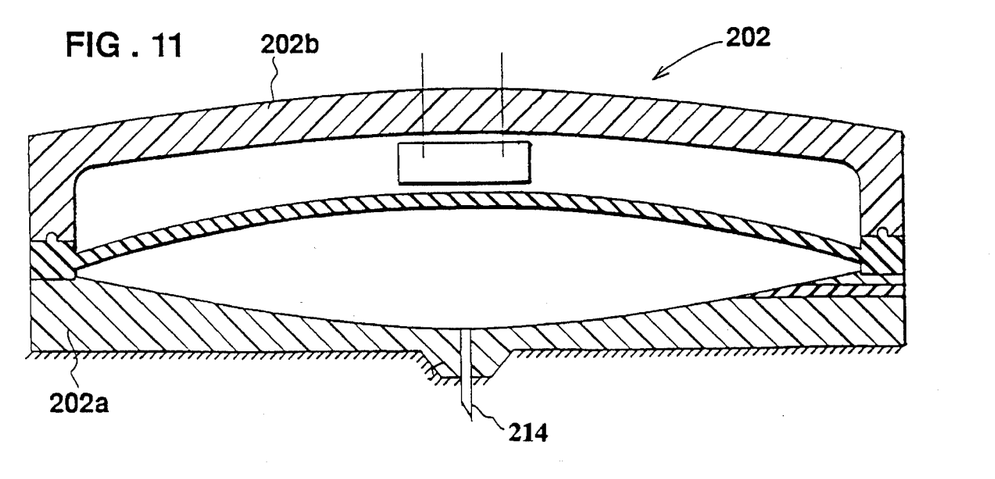

THE EMBODIMENTS OF FIGS. 10 AND 11

While in the above-described embodiments, the lower surface of the housing (e.g., 4) is flat, FIGS. 10 and 11 illustrate variations in this construction. Thus, FIG. 10 illustrates the housing 102 having a housing section 102a of convex configuration on the lower surface 104 and coated with the pressure-sensitive adhesive 106. A diaphragm 108 divides the interior of the housing into a drug reservoir 110 and a gas chamber 112 containing an electrolytic cell gas generator 116. The hollow needle 114 extends through the center of the lower surface 104 of the housing, and is dimensioned as described above to penetrate through the epidermis of the subject's skin. FIG. 11 illustrates a similar construction, except that the housing section 202a of the housing 202 is formed with a central projection 202c through which the hollow needle 214 extends.

The constructions of FIGS. 10 and 11 counteract the natural resilience or stretching of the skin when the device is applied, so as to achieve penetration of the epidermis by the needle. The use of a narrow diameter hollow needle minimizes trauma, minimizes leakage, and better ensures more controlled delivery.

THE EMBODIMENT OF FIG. 14

FIG. 14 illustrates an embodiment having housing 302 and a membrane 315, which is permeable to the liquid drug and impermeable to solid impurities and covers the inner end of hollow needle 314. For illustration purposes, the membrane is shown in an embodiment similar to the embodiment shown in FIG. 10. However, the membrane can be present in any embodiment according to the present invention.

EXAMPLE 1

Figure 12:
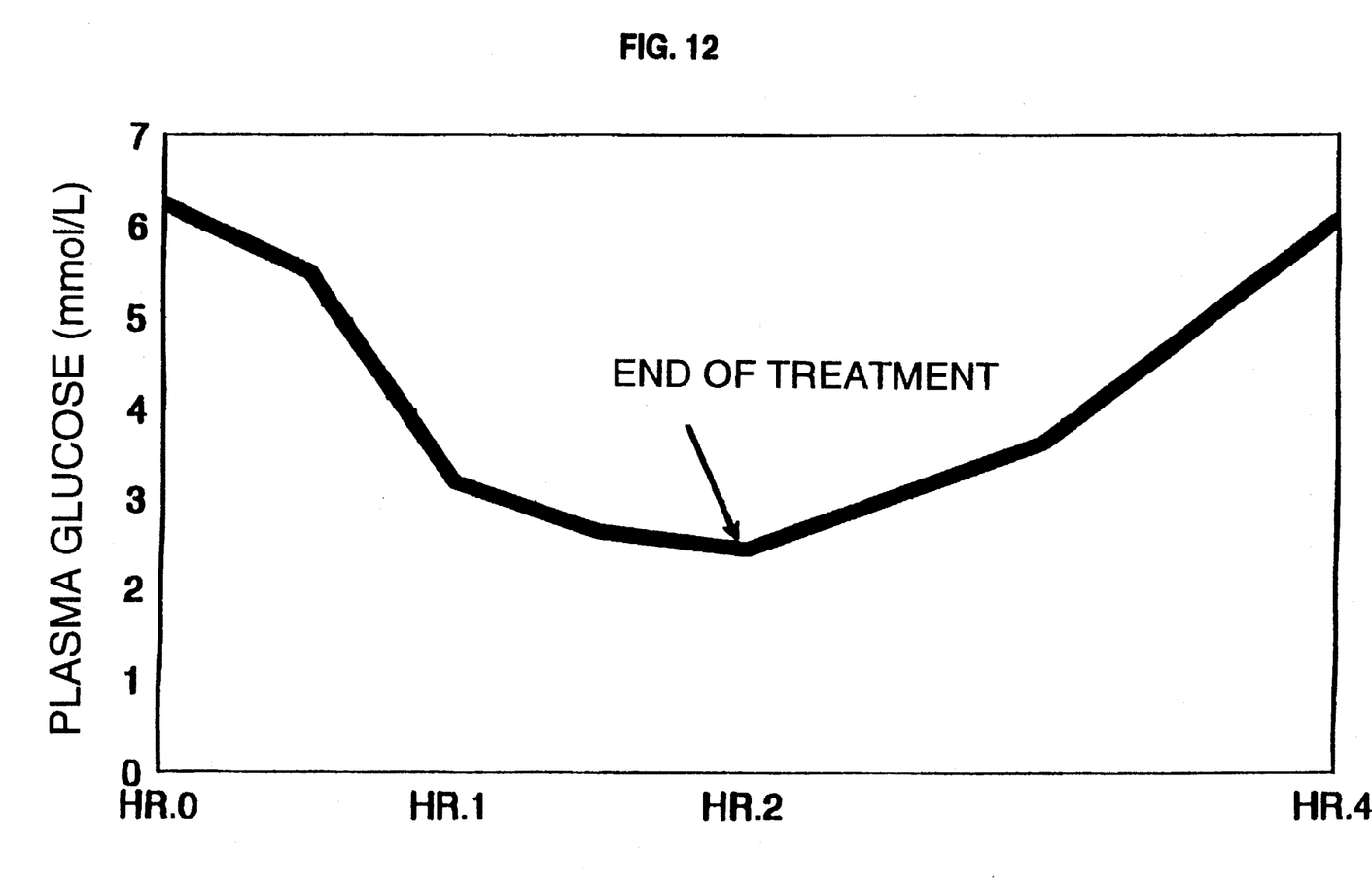
FIGS. 12 and 13 show delivery characteristics of insulin and salmon calcitonin, respectively, from a device constructed in accordance with the invention.

A device according to the instant invention containing 0.6 ml of a solution of insulin (100 I.U./ml) was affixed to each of two rabbits and the devices were switched on. The insulin solution was infused at a rate of 0.1 ml/hour for two hours. As shown in FIG. 12, blood glucose concentrations for these rabbits were measured at various times following activation of the devices. At one hour, mean blood glucose concentration had fallen from a control value of 6.25 mmol/l to 3.2 mmol/l. This value stayed relatively constant at 1.5 hours following activation (2.65 mmol/l) and at 2 hours (2.5 mmol/l), at which time the devices were removed. One hour later the mean value was 3.7 mmol/l, which value continued to rise with time.

EXAMPLE 2

Figure 13:
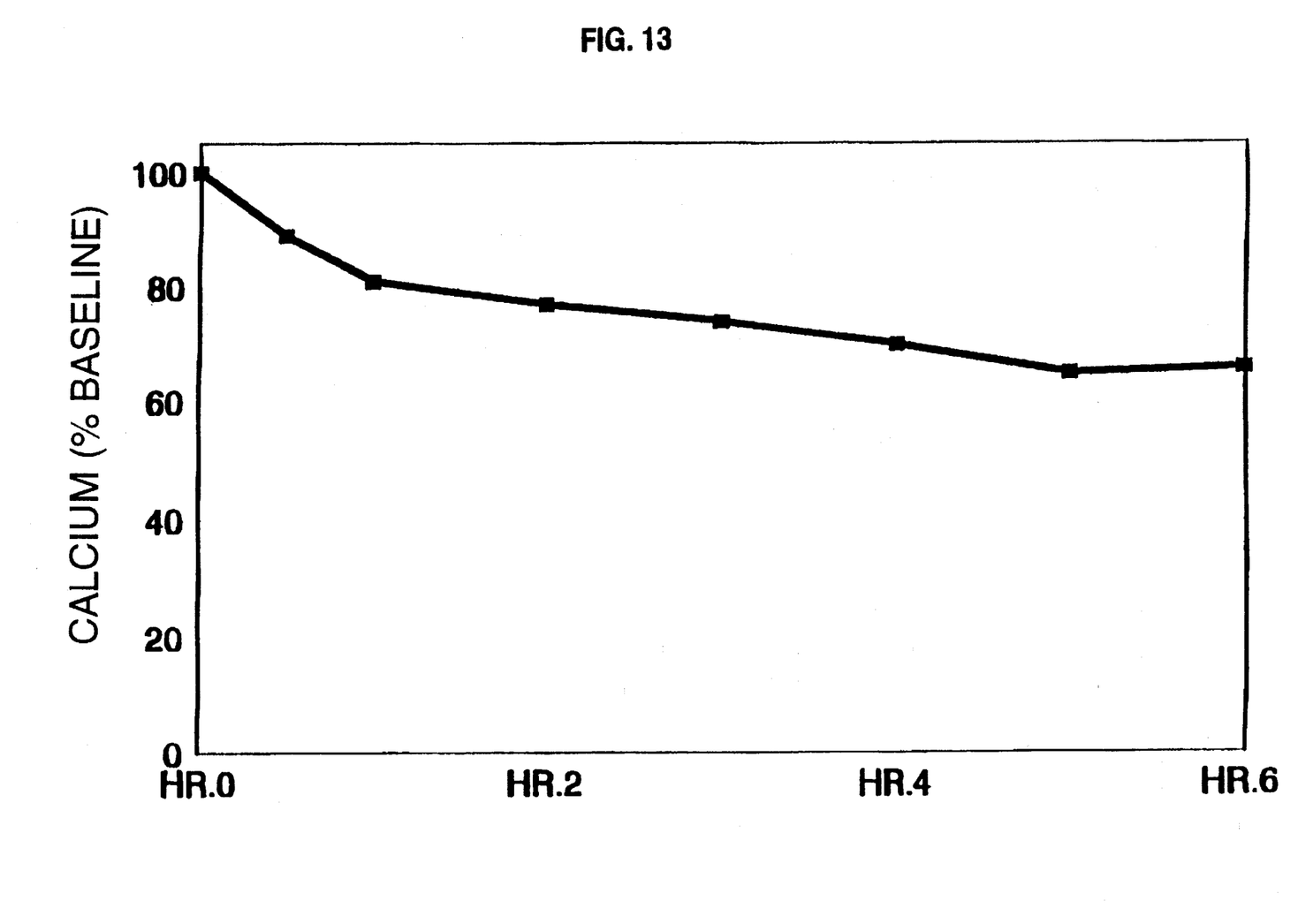

A device according to the instant invention containing 0.6 ml of a solution of salmon calcitonin (1.0 mg/ml) was affixed to each of four rabbits. This solution was infused at the rate of 0.1 ml/hour for 6 hours. Serum calcium concentrations were measured via an ear vein at 0, 0.5, 1, 2, 3, 4, 5, and 6 hours following activation of the device, at which point the device was removed. As shown in FIG. 13, mean calcium concentrations fell steadily throughout the period of application and reached values representing 62.5% and 66.6% of the control values at 5 and 6 hours respectively.

While the invention has been described with respect to several preferred embodiments, it well be appreciated that these are set forth merely for purposes of example, and that many other variations, modifications and applications of the invention may be made.

What is claimed:

1. An intradermal drug delivery device for delivering a liquid drug to a subject via the subject's skin, comprising:
   (a) a housing having a lower surface for application to the skin of the subject;
   (b) means for affixing the housing in position with the lower surface in contact with the subject's skin;
   (c) a drug reservoir within the housing, wherein the reservoir is in the form of an expansible-contractible chamber which is expanded when filled with the drug and which can be contracted to dispense the drug therefrom;
   (d) a single hollow needle associated with the drug reservoir extending through the lower surface, having an inner end communicating with the drug reservoir and an outer end projecting outwards a sufficient distance so as to penetrate through the epidermis and into the dermis when the housing is pressed against the skin; and
   (e) means for actively discharging the drug from the reservoir to the subject's skin via the needle;
wherein the lower surface is shaped such that when it is pressed against the skin a substantial proportion of the pressure applied to the skin is directed through the needle tip.

2. The device according to claim 1, wherein the means for affixing the housing in position comprises a pressure-adhesive coating on the lower surface thereof.

3. The device according to claim 1, wherein the lower surface of the housing is flat.

4. The device according to claim 1, wherein the lower surface of the housing has a convex shape and the hollow needle extends from the center of the convexity.

5. The device according to claim 1, wherein the lower surface of the housing is provided with a protuberance from which the needle projects.

6. The device according to claim 1, wherein the lower surface of the housing is of a conical shape and the hollow needle extends from the apex of the cone.

7. The device according to claim 1, wherein the needle projects outwards of the housing by 0.3–3.0 mm and has an outer diameter of 0.1–0.2 mm and an inner diameter of 0.05–0.075 mm.

8. The device according to claim 7, wherein the needle projects outwards of the housing by 0.3–1.0 mm.

9. The device according to claim 1, wherein the drug reservoir, when filled, has a volume from about 0.2 ml to 10.0 ml.

10. The device according to claim 9, wherein the drug reservoir has a volume from about 0.5 ml to 3.0 ml.

11. The device according to claim 1, wherein the means for actively discharging the drug comprises an electrically controlled gas generator within the housing for generating a gas to contract the drug reservoir in order to discharge the drug therefrom.

12. The device according to claim 11, wherein the gas generator is an electrolytic cell.

13. The device according to claim 11, further comprising a start button which is depressible in order to energize the gas generator and thereby to start discharging the drug from the drug reservoir.

14. The device according to claim 11, further comprising an electronic circuit for controlling the time and rate of gas generation, thereby controlling the discharge of the drug from the drug reservoir.

15. The device according to claim 14, wherein the electronic circuit comprises a microprocessor which is programmable with respect to the time and rate of gas generation.

16. The device according to claim 11, wherein the housing includes a plurality of drug reservoirs, each reservoir being contractible by a separate gas generator and communicating with an outlet cavity with which the single hollow needle also communicates.

17. The device according to claim 16, wherein all the drug reservoirs communicate in series with the outlet cavity.

18. The device according to claim 16, wherein all the drug reservoirs communicate in parallel with the outlet cavity.

19. The device according to claim 1, wherein the housing includes a plurality of drug reservoirs, each having a single hollow needle associated therewith.

20. The device according to claim 19, wherein each drug reservoir delivers a different liquid drug to the subject.

21. The device according to claim 1, wherein the housing further includes a sensor for detecting a condition in the body of the subject and for controlling the delivery of the drug in response thereto.

22. The device according to claim 21, wherein the sensor is a temperature sensor for sensing the temperature of the subject and for controlling the delivery of the drug in response thereto.

23. The device according to claim 21, wherein the sensor is a pulse rate sensor for sensing the pulse rate of the subject and for controlling the delivery of the drug in response thereto.

24. The device according to claim 21, wherein the sensor is a blood glucose sensor for sensing the blood glucose level of the subject and controlling the delivery of the drug in response thereto.

25. The device according to claim 21, wherein the sensor is a blood pressure sensor for sensing the blood pressure of the subject and controlling the delivery of the drug in response thereto.

26. The device according to claim 21, wherein the sensor is a pH sensor for sensing the pH of a body fluid of the subject and controlling the delivery of the drug in response thereto.

27. The device according to claim 1, which further comprises a membrane which is permeable to the liquid drug and impermeable to solid impurities, the membrane covering the inner end of the hollow needle.

28. The device according to claim 29, wherein the drug is selected from the group consisting of peptides, proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, antineoplastics, prostaglandins and antidiuretic agents.

29. The device according to claim 1, further comprising at least one liquid drug contained in the drug reservoir.

30. A method of delivering a biologically effective amount of at least one liquid drug Intradermally to a subject, comprising the steps of:
  (1) affixing the intradermal drug delivery device according to claim 1 to the skin of the subject such that the needle penetrates through the epidermis and into the dermis, wherein the drug reservoir contains a biologically effective amount of at least one liquid drug; and
  (2) activating the means for actively discharging the at least one drug so as to deliver a biologically effective amount of the at least one drug to the subject.

31. The method according to claim 30, wherein the drug is selected from the group consisting of peptides, proteins, hormones, analgesics, anti-migraine agents, anti-coagulant agents, anti-emetic agents, cardiovascular agents, anti-hypertensive agents, anti-depressants, narcotic antagonists, chelating agents, anti-anginal agents, chemotherapy agents, sedatives.

32. An intradermal drug delivery device for delivering a liquid drug to a subject via the subject's skin, comprising:
  (a) a housing having a lower surface for application to the skin of the subject;
  (b) means for affixing the housing in position with the lower surface in contact with the subject's skin;
  (c) a drug reservoir within the housing;
  (d) a single hollow needle associated with the drug reservoir extending through the lower surface, having an inner end communicating with the drug reservoir and an outer end projecting outwards a sufficient distance so as to penetrate through the epidermis and into the dermis when the housing is pressed against the skin; and
  (e) means for actively discharging the drug from the reservoir to the subject's skin via the needle, wherein the means for actively discharging the drug comprises an electrically controlled gas generator within the housing for generating a gas to contract the drug reservoir in order to discharge the drug therefrom;
wherein the lower surface is shaped such that when it Is pressed against the skin a substantial proportion of the pressure applied to the skin is directed through the needle tip.

33. The device according to claim 32, wherein the reservoir is in the form of an expansible-contractible chamber which is expanded when filled with the drug and which can be contracted to dispense the drug therefrom.

34. The device according to claim 33, wherein the means for actively discharging the drug comprises a spring which is stressed by the expansion of the drug reservoir upon filling it with a drug, and which tends to return to its unstressed condition to contract the reservoir and thereby to discharge the drug via the hollow needle.

35. The device according to claim 33, wherein the means for actively discharging the drug comprises a membrane which is stressed by the expansion of the drug reservoir upon filling it with a drug, and which tends to return to its unstressed condition to contract the reservoir and thereby to discharge the drug via the hollow needle.

36. The device according to claim 33, wherein the means for actively discharging the drug comprises a deformable liquid-impermeable membrane, and a rigid liquid-permeable membrane; one side of the deformable liquid-impermeable membrane defining one side of the drug reservoir; the opposite side of the deformable liquid-impermeable membrane and one side of the rigid liquid-permeable membrane defining a saline reservoir for receiving a saline solution; the opposite side of the rigid liquid-permeable membrane defining, with a rigid part of the housing, a pure water reservoir for receiving pure water to expand the saline reservoir by osmosis, thereby to contract the drug reservoir in order to dispense the drug therefrom via the hollow needle.

37. An intradermal drug delivery device for delivering a liquid drug to a subject via the subject's skin, comprising:
  (a) a housing having a lower surface for application to the skin of the subject;
  (b) means for affixing the housing in position with the lower surface in contact with the subject's skin;
  (c) a drug reservoir within the housing;
  (d) a single hollow needle associated with the drug reservoir extending through the lower surface, having an inner end communicating with the drug reservoir and an outer end projecting outwards a sufficient distance so as to penetrate through the epidermis and into the dermis when the housing is pressed against the skin; and
  (e) means for actively discharging the drug from the reservoir to the subject's skin via the needle;
wherein the lower surface is shaped such that when it is pressed against the skin a substantial proportion of the pressure applied to the skin is directed through the needle tip and wherein the lower surface of the housing is provided with a protuberance from which the needle projects.

* * * * *